United States Patent [19]

Saito et al.

[11] Patent Number: 5,248,828
[45] Date of Patent: Sep. 28, 1993

[54] METHOD FOR PREPARING SULFONES

[75] Inventors: Toranosuke Saito; Shigeru Oda; Hiroki Tsunomachi; Daishiro Kishimoto, all of Osaka, Japan

[73] Assignee: Sanko Kaihatsu Kagaku Kenkyusho, Osaka, Japan

[21] Appl. No.: 896,313

[22] Filed: Jun. 10, 1992

Related U.S. Application Data

[62] Division of Ser. No. 864,841, Apr. 7, 1992.

[30] Foreign Application Priority Data

Apr. 12, 1991 [JP] Japan ................................ 3-106411

[51] Int. Cl.$^5$ ............................................. C07C 315/04
[52] U.S. Cl. .................................... 568/33; 568/30; 558/48; 558/56; 558/51
[58] Field of Search ...................... 568/33, 30, 56, 48, 568/51

[56] References Cited

FOREIGN PATENT DOCUMENTS 1298822 12/1972 United Kingdom .

OTHER PUBLICATIONS

Mar., *Advanced Organic Chemistry*, 3rd Edition, p. 444, 1985.
Poly(arylene ether sulphones) by polyetherification: 1. Synthesis of halogenophenols* by T. E. Attword, et al., Polymer, 1977, vol. 18, Apr.

*Primary Examiner*—Marianne M. Cintins
*Assistant Examiner*—Margaret J. Page
*Attorney, Agent, or Firm*—Baker & Daniels

[57] ABSTRACT

A method for preparing a sulfone represented by the following formula:

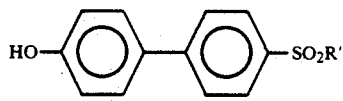

wherein R' represents a lower alkyl group, an aryl group or an aryl group whose nucleus has at least one substituent selected from the group consisting of a halogen atom, nitro group, a lower alkyl group, phenyl group and a phenyl group substituted with a halogen atom, or an alkali metal salt thereof. A sulfonic acid ester of 4-hydroxybiphenyl is condensed at a temperature of 0° to 200° C. in a presence of a Lewis acid or a super-strong acid with a sulfonyl chloride represented by the formula R'SO$_2$Cl, wherein R' is the same as that defined above.

4 Claims, No Drawings

METHOD FOR PREPARING SULFONES

This is a division of application Ser. No. 07/864,841, filed Apr. 7, 1992.

BACKGROUND OF THE INVENTION (a) Field of the Invention

The present invention relates to a method for preparing sulfones. The sulfones prepared by the method of the present invention are characterized by having bisphenyl skeletons, effectively used as materials for preparing, for instance, synthetic resins, dyes, surfactants, agricultural chemicals and medicines as well as developers for recording paper and, in particular, the synthetic resins derived from these sulfones are characterized by and excellent in high transparency, heat resistance and impact resistance.

(b) Description of the Prior Art

Methods for preparing sulfones as contemplated by the present invention are disclosed in U.K. Patent No. 1,298,822 and Polymer, 1977, 18 (April), p. 354.

In the method as disclosed in U.K. Patent No. 1,298,822, 4-nitrobiphenyl is used as a starting material and the method comprises a relatively large number of steps. For this reason, it suffers from the problem of high production cost. Further the carcinogenicity of 4-nitrobiphenyl has been talked about. Therefore, it would not always be an industrially excellent method. On the other hand, the method disclosd in Polymer, 1977, 18 (April), p. 354 utilizes carbonate of 4-hydroxybiphenyl as a starting material. However, this method likewise suffers from the problems in that the production of the carbonate is quite troublesome and that a relatively large amount of an organic solvent having a high boiling point must be used during the condensation reaction because of the relatively high melting point of the carbonate.

SUMMARY OF THE INVENTION

Accordingly, the object of the present invention is to provide an improved, relatively simple method for preparing sulfones having biphenyl skeletons which can be effectively used as materials for preparing, for instance, synthetic resins, dyes, surfactants, agricultural chemicals and medicines as well as developers for recording paper and, in particular, can provide synthetic resins having high transparency, heat resistance and impact resistance.

The foregoing object of the present invention can effectively be accomplished by providing a method for preparing sulfones represented by the following general formula (1):

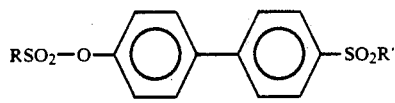

(1)

(wherein R represents a lower alkyl group, an aryl group or an aryl group whose nucleus has substituents; and R' may be identical to or different from R and represents a lower alkyl group, an aryl group or an aryl group whose nucleus has substituents) which comprises the step of condensing sulfonic acid esters of 4-hydroxybiphenyl represented by the following general formula (2):

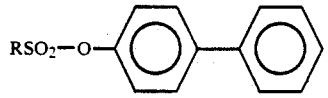

(2)

(wherein R is the same as that defined above) with sulfonyl chlorides represented by the following general formula (3):

$$R'SO_2Cl \qquad (3)$$

(wherein R' is the same as that defined above) in the presence of a Lewis acid or a superstrong acid; or a method for preparing sulfones represented by the following general formula (4):

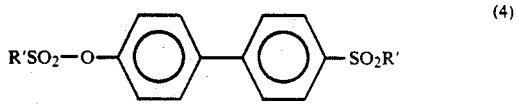

(4)

(wherein R' is the same as that defined above) which comprises the step of condensing 4-hydroxyphenyl with sulfonyl chlorides represented by the following general formula (3):

$$R'SO_2Cl \qquad (3)$$

(wherein R' is the same as that defined above) in the presence of a Lewis acid or a superstrong acid; or a method for preparing sulfones or alkali salts thereof represented by the following general formula (5):

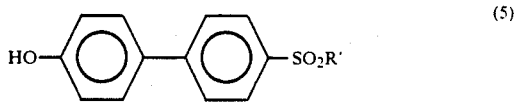

(5)

(wherein R' is the same as that defined above) which comprises the step of saponifying sulfones represented by the following general formula (6):

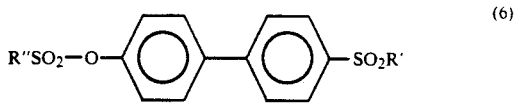

(6)

(wherein R" is identical to R or R' which may be the same or different and each represents a lower alkyl group, an aryl group or an aryl group whose nucleus has substituents) in the presence of an acid or alkali.

According to the present invention, sulfones contemplated by the present invention can relatively easily be prepared from starting materials industrially easily available through relatively simple processes in a high yield. This is resulted from the fact that sulfonic acid esters of 4-hydroxybiphenyl exhibit a high degree of orientation at the 4'-position during the Friedel-Crafts condensation reaction and hence a high selectivity to the intended compounds during the condensation reaction.

DESCRIPTION OF THE PREFERRED EMBODIMENTS

In the foregoing general formulae (1) to (6), the substituents R, R' and R" may be the same or different and each represents a lower alkyl group, an aryl group or an aryl group whose nucleus has substituents. Specific examples thereof preferably used in the practice of the present invention include methyl, ethyl, propyl, phenyl, 4-fluorophenyl, 4-chlorophenyl, 4-bromophenyl, 3-nitrophenyl, 4-methylphenyl, 2,4-dimethylphenyl, 2,5-dimethylphenyl, 3,4-dimethylphenyl, 4-ethylpheny, 4-isopropylphenyl, 4-biphenylyl, 4'-chloro-4-biphenylyl, 4'-bromo-4-biphenylyl, 1-naphthyl or 2-naphthyl groups. The sulfone in which R and R' each represents a 4-chlorophenyl group or R represents methyl group and R' represents a 4-chlorophenyl group is preferable.

The sulfonic acid esters of 4-hydroxybiphenyl represented by the general formula (2) can easily be prepared by methods already well-known in the art. An example of such methods comprises condensing 4-hydroxybiphenyl with corresponding sulfonyl chlorides in the presence of a basic compound, a Lewis acid or a superstrong acid. Another example thereof comprises subjecting, to an ester interchange reaction, sulfonic acid esters of lower phenols and 4-hydroxybiphenyl in the presence of a basic compound, a Lewis acid or a superstrong acid.

Preferred examples of the basic compounds used in the foregoing methods include sodium hydroxide, potassium hydroxide, sodium carbonate, potassium carbonate, trimethylamine, triethylamine, pyridine and picoline. Preferred examples of the Lewis acids usable in these methods include boron trifluoride, magnesium chloride, aluminum choride, titanium chloride, ferric chloride, zinc chloride and tin chloride. Preferred examples of the superstrong acids usable in these methods include fluorosulfonic acid, trifluoromethanesulfonic acid, pentafluoroethanesulfonic acid, phosphomolybdic acid, silicomolybdic acid, phosphotungstic acid and silicotungstic acid.

The condensation reaction may be performed in the presence or absence of an aqueous medium or an inert solvent, but the condensation reaction carried out in the presence of a Lewis acid or a superstrong acid is a catalytic dehydrochlorination reaction and the reaction smoothly proceeds in the presence of a small amount of an inert solvent or in the absence of any solvent. Specific examples of inert solvents usable in the reaction include chloroform, carbon tetrachloride, dichloroethane, trichloroethane, benzene, toluene, xylene, chlorobenzene, dichlorobenzene, trichlorobenzene, nitrobenzene, sulfolane, diphenylsulfone, tetrahydrofuran and dioxane. The ester interchange reaction proceeds smoothly and completely if it is carried out while removing lower phenols simultaneously produced during the reaction by distillation under a reduced pressure. Such lower phenols include, for instance, phenol, o-cresol, m-cresol and p-cresol. Typical examples of the sulfonic acid esters of 4-hydroxybiphenyl represented by the general formula (2) include 4-biphenylylmethanesulfonate (methanesulfonic acid ester of 4-hydroxybiphenylyl), 4-biphenylylethanesulfonate, 4-biphenylylbenzenesulfonate, 4-biphenyly (p-chlorobenzene)sulfonate, 4-biphenylyl(p-bromobenzene)sulfonate, 4-biphenyly(p-toluene)sufonate and 4-biphenylyl(4'-bromo-4-biphenyl)sulfonate.

The condensation reaction of sulfonic acid esters of 4-hydroxybiphenyl represented by Formula (2) with sulfonyl chlorides of Formula (3) in the presence of a Lewis acid or a superstrong acid can be referred to as a Friedel-Crafts condensation reaction. Specific examples of the sulfonyl chlorides of Formula (3) include methanesulfonyl chloride, ethanensulfonyl chloride, propanesulfonyl chloride, benzenesulfonyl chloride, p-fluorobenzenesulfonyl chloride, p-chlorobenzenesulfonyl chloride, p-bromobenzenesulfonyl chloride, m-nitrobenzenesulfonyl chloride, p-toluenesulfonyl chloride, 2,4-xylenesulfonyl chloride, 2,5-xylenesulfonyl chloride, 3,4-xylenesulfonyl chloride, p-ethylbenzenesulfonyl chloride, p-cumenesulfonyl chloride, 4-biphenylsulfonyl chloride, 4'-chloro-4-biphenylsulfonyl chloride, 4'-bromo-4-biphenylsulfonyl chloride, 1-naphthalenesulfonyl chloride and 2-naphthalenesulfonyl chloride. Preferred Lewis acids used herein include aluminum chloride, ferric chloride and zinc chloride The superstrong acids herein referred to are, for instance, superstrong acids such as fluorosulfonic acid, trifluoromethanesulfonic acid and pentafluoroethanesulfonic acid; and heteropoly-acids such as phosphomolybdic acid, silicomolybdic acid, phosphotungstic acid and silicotungstic acid. These superstrong acids are preferably used in the form of anhydrides. These catalysts, i.e., these Lewis acids and superstrong acids are used in an amount ranging from 0.1 to 300 mole % on the basis of the amount of the sulfonic acid ester of 4-hydroxybiphenyl or sulfonyl chloride.

The condensation reaction of the sulfonic acid esters of 4-hydroxybiphenyl with the sulfonyl chlorides in the presence of a Lewis acid or a superstrong acid is a dehydrochlorination condensation reaction and theoretically performed by reacting equimolar amounts of these compounds, but it is generally preferred to carry out the reaction under the condition of a slight excess of the sulfonyl chloride. The reaction temperature preferably ranges from 0° to 200° C. and more preferably ranges from 50° to 150° C. within which the reaction smoothly proceeds. If the reaction temperature is too low, the viscosity of the reaction system is extremely high and as a result, it is sometimes observed that the condensation reaction does not smoothly proceed. In this case, an inert solvent can be added to reduce the viscosity of the system and to thus make the progress of the reaction smooth. Specific examples of inert solvents used include hexane, heptane, octane, cyclohexane, benzene, toluene, xylene, carbon tetrachloride, dichloroethane, vinylidene chloride, 1,2-dichloroethylene, trichloroethylene, tetrachloroethylene, chlorobenzene, 4-chlorotoluene, nitromethane, nitroethane, nitropropane, nitrobenzene and diphenylsulfone.

The process for the condensation reaction of 4-hydroxybiphenyl with sulfonyl chloride of Formula (3) performed in the presence of a Lewis acid or a superstrong acid comprises two steps from the chemical standpoint. The first step is an ester condensation reaction of 4-hydroxybiphenyl with sulfonyl chlorides and completed at a lower temperature within a short time period. While the second step is a Friedel-Crafts condensation reaction of the sulfonic acid esters of 4-hydroxybiphenyl produced in the first step with sulfonyl chlorides and can be conducted in the manner discussed above. Both of these steps are dehydrochlorination condensation reactions and can smoothly proceed in the presence of a single or combined catalyst system It is theoretically a matter of course that 4-hydroxybiphenyl and the sulfonyl chlorides are reacted in a molar ratio of ½, but it is preferred to react these in a molar ratio smaller than that defined above. Specific examples of sulfonyl chlorides of Formula (3), Lewis acids and superstrong acids are the same as those listed above.

The sulfones represented by Formula (6) are saponified in the presence of an acid or alkali to thus give sulfones represented by Formula (5) or alkali salts thereof which are more useful from the industrial standpoint. The saponification reaction with an alkali is represented by the following reaction scheme:

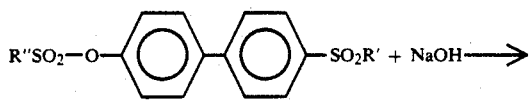

or

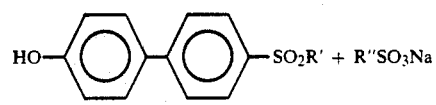

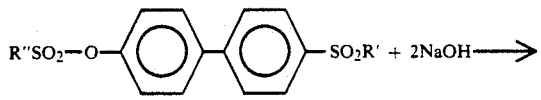

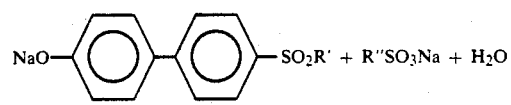

The reaction requires at least one equivalent of an alkali per mole of sulfones. In particular, the saponification reaction proceeds under mild conditions, for instance, at a temperature of not more than 100° C., the alkali is preferably used in an amount of at least 2 equivalents per mole of the sulfones according to the latter reaction scheme. Specific examples of preferred alkalis are sodium hydroxide and potassium hydroxide. The saponification reaction is preferably conducted in an aqueous medium and more preferably the aqueous medium is employed in combination with a water-soluble inert solvent for the purposes of smoothening the saponification reaction and of making the reaction system uniform. Specific examples of such water-soluble inert solvents are isopropanol, tertiary butanol, tertiary amyl alcohol, tetrahydrofuran, 1,4-dioxane, ethylene glycol dimethyl ether, diethylene glycol dimethyl ether, diethylene glycol diethyl ether and sulfolane. If an alkali is used in an amount on the order of about one equivalent per mole of the sulfones as in the former reaction scheme and the reaction temperature is not more than 100° C., it takes a very long time till the reaction is completed. Preferably the reaction is conducted at a temperature ranging from 100° to 200° C. under pressure since the reaction rapidly proceeds. In this case, the simultaneous use of an aqueous medium and a water-soluble inert solvent are likewise preferred.

The saponification reaction of the sulfones represented by Formula (6) performed in the presence of an acid is usually referred to as "hydrolysis reaction" and represented by the following reaction scheme:

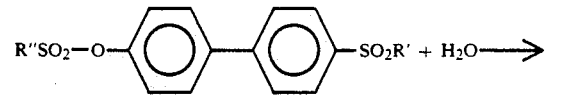

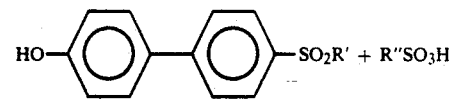

In this case, the acid used simply serves as a catalyst and it is sufficient to use the acid in an amount ranging from 0.01 to 0.5 e.g. per mole of the sulfones used. In this case, the simultaneous use of an aqueous medium and a water-soluble inert solvent is likewise preferred. Specific examples of acids include sulfuric acid, trifluoromethanesulfonic acid, pentafluoroethanesulfonic acid, benzenesulfonic acid, 4-chlorobenzenesulfonic acid, phosphomolybdic acid, silicomolybdic acid, phosphotungstic acid and silicotungstic acid and specific examples of water-soluble inert solvents are the same as those listed above in connection with the saponification with an alkali. In addition, the reaction temperature preferably ranges from 80° to 200° C. while the application of a pressure is sometimes required depending on the temperature employed.

The sulfones obtained according to the method of the present invention may be purified for further improvement of the quality thereof depending on the intended applications. A part of the sulfones can be purified through vacuum distillation, but most of the sulfones can easily be crystallized. Therefore, sulfones of high quality can be obtained through recrystallization from water or organic solvents. The sulfones may be recrystallized from a wide variety of solvents selected depending on physical properties of each particular sulfone.

The present invention will hereinafter be explained in more detail with reference to the following non-limitative working Examples for making the content of the present invention more clearer.

EXAMPLE 1-1

To a 5,000 ml inner volume, four-necked flask of hard glass equipped with a stirring machine, a thermometer, a dropping funnel and a reflux condenser, there were added 3,000 g of water, 340 g (2 moles) of 4-hydroxybiphenyl and 118 g (2.1 moles) of potassium hydroxide, the contents of the flask were maintained at 50° C. with stirring and then 229 g (2 moles) of methanesulfonyl chloride was dropwise added thereto over 2 hours through the dropping funnel. After the dropwise addition, the contents of the flask were maintained at that temperature for additional one hour and then cooled down to 30° C. The contents were filtered off and the resulting filter cake was washed with 1,000 g of water. After drying the filter cake, it was recrystallized from toluene to give 421 g of white crystalline powder. The product had a melting point of 153° C. and a sulfur content of 12.8% and gas chromatography measurement indicated that it was a single compound. These facts clearly indicate that the product is an intended compound, i.e., a methanesulfonic acid ester of 4-hydroxybiphenyl.

EXAMPLE 1-2

To a 2,000 ml inner volume, four-necked flask equipped with a stirring machine, a thermometer, a dropping funnel and a reflux condenser, there were added 1,000 g of dichloroethane, 248 g (1 mole) of the methanesulfonic acid ester of 4-hydroxybiphenyl prepared in Example 1-1 and 174 g (1.3 mole) of anhydrous aluminum chloride and then 120 g (1.05 mole) of methanesulfonyl chloride was dropwise added to the contents of the flask over about one hour through the dropping funnel with stirring. The temperature of the contents was maintained at 30° C. during the dropwise addition. Immediately after the dropwise addition, the contents of the flask were heated so that they boiled gently. Hydrogen chloride gas came out through the top of the reflux condenser during the heat treatment and was properly treated. The generation of hydrogen chloride gas was stopped and the reaction was completed after holding the contents under these conditions for 48 hours. To a 5,000 ml inner volume beaker of hard glass, there were added 1,000 g of water and 1,000 g of crushed ices and the foregoing reaction mixture was poured into the ice water in the beaker with vigorous stirring. After stirring for about 2 hours, the contents of the beaker were filtered off and the resulting filter cake was washed with 1,000 g of water. After drying the filter cake, it was recrystallized from xylene to give 295 g of white crystalline powder. The product had a melting point of 205° C. and a sulfur content of 19.4% and gas chromatography measurement indicated that it was a single compound. These data clearly indicate that the product is the intended compound, i.e., methanesulfonic acid ester of 4-hydroxy-4'-methanesulfonylbiphenyl.

EXAMPLE 2

To a 2,000 ml inner volume, four-necked flask of hard glass equipped with a stirring machine, a thermometer, a dropping funnel and a reflux condenser, there were added 400 g of water, 300 g of dioxane, 42 g (1.05 mole) of sodium hydroxide and 163 g (0.5 mole) of the methanesulfonic acid ester of 4-hydroxy-4'-methanesulfonylbiphenyl prepared in Example 1-2 and then the contents of the flask were heated so that they boiled gently. The contents were maintained under these conditions over about 2 hours and 140 ml of 4N hydrogen chloride aqueous solution was dropwise added to the contents over about one hour through the dropping funnel. Then the contents were cooled down to 30° C. or lower, were filtered off and the resulting filter cake was washed with 500 g of water. After drying the filter cake, it was recrystallized from xylene to give 242 g of white crystalline powder. The product had a melting point of 195° C. and a sulfur content of 12.7% and gas chromatography measurement indicated that it was a single compound. These data clearly indicate that the product is the intended compound, i.e., 4-hydroxy-4'-methanesulfonylbiphenyl.

EXAMPLE 3

To a 2,000 ml inner volume, four-necked flask of hard glass equipped with a stirring machine, a thermometer, a reflux condenser and an inlet port, there were added 510 g (3 moles) of 4-hydroxybiphenyl, 1,091 g (6.18 moles) of benzenesulfonyl chloride, 100 g of dichloroethane and 1.3 g (0.01 mole) of zinc chloride and then the contents of the flask were heated to 80° C. with stirring. Hydrogen chloride gas came out through the top of the reflux condenser during the heat treatment and was properly treated. After holding the contents at 80° C. for about 4 hours, only a small amount of hydrogen chloride gas was generated. At this stage, a small amount of the contents were withdrawn from the flask and purified to give white crystalline powder which had a melting point of 102° C. and a sulfur content of 10.5% and which was a single compound as confirmed by gas chromatography. This clearly indicates that the compound is benzenesulfonic acid ester of 4-hydroxybiphenyl.

Then 5 g (0.03 mole) of anhydrous ferric chloride was added to the contents through the inlet port. When the temperature of the contents was raised up to 120° C., the generation of hydrogen chloride gas was again started. The generation of hydrogen chloride gas was stopped and the reaction was completed after holding the contents at that temperature for 24 hours. The resulting reaction mixture was poured into a 5,000 inner volume flask containing 200 ml of a 5N hydrochloric acid solution and 2,500 g of toluene with vigorous stirring and the contents of the flask were heated to 80° C. After about one hour, the reaction system was allowed to stand to remove the aqueous phase. It was further washed 3 times with 200 g each of water, followed by dehydration through azeotropic distillation of the toluene solution and cooling while gently stirring to give white crystals. The contents were cooled down to 10° C., filtered off through suction filtration and the resulting filter cake was washed with 1,000 g of toluene and dried to give 1,120 g of white crystals. The product had a melting point of 138° C. and a sulfur content of 14.2% and gas chromatography measurement indicated that it was a single compound. These data clearly indicate that the product is the intended compound, i.e., benzenesulfonic acid ester of 4-hydroxy-4'-benzenesulfonylbiphenyl.

EXAMPLE 4

To a 1,000 ml volume stainless steel autoclave, there were added 500 ml of water, 21 g (0.525 mole) of sodium hydroxide and 225 g (0.5 mole) of benzenesulfonic acid ester of 4-hydroxy-4'-benzenesulfonylbiphenyl obtained in Example 3 and then the temperature of the contents was raised up to 180° C. with stirring. At this stage, the pressure in the autoclave was about 10 kgf/cm². The contents were maintained at that temperature for about 2 hours, followed by cooling of the autoclave and the removal of the contents. To the contents, there was added 5 ml of a 10N hydrochloric acid solution and the mixture was subjected to suction filtration to give a filter cake. The cake was washed with 300 g of water, then dried and recrystallized from dimethylformamide to give 104 g of white crystalline powder. The product had a melting point of 217° C., a sulfur content of 10.3% and a hydroxyl value of 181 and gas chromatography measurement indicated that it was a single compound. These data clearly indicate that the product is the intended compound, i.e., 4-hydroxy-4'-benzenesulfonylbiphenyl.

EXAMPLE 5

To a 2,000 ml inner volume, four-necked flask equipped with a stirring machine, a thermometer, a reflux condenser and an inlet port, there were added 1,000 g of dichloroethane, 227 g (0.07 mole) of p-toluenesulfonic acid ester of 4-hydroxybiphenyl having a melting point of 184° C. and prepared in the same manner used in Example 1-1, 140 g (0.735 mole) of p-toluenesulfonyl chloride and 121.5 g (0.91 mole) of anhydrous aluminum chloride and the contents were heated with stirring so that they gently boiled After about 30 munites, the generation of hydrogen chloride gas wa stopped and the condensation reaction was completed. To a 5,000 ml inner volume flask, there were added 1,000 g of water and 1,000 g of crushed ices and the condensation reaction mixture was poured into the resulting ice water with vigorous stirring. After stirring for about 2 hours, the temperature of the contents reached about 30° C. The contents were subjected to suction filtration. The resulting filter cake was washed with 300 g of water, dried and purified through recrystallization from xylene to give 315 g of white crystalline powder. The product had a melting point of 181° C. and a sulfur content of 13.3% and gas chromatography measurement indicated that it was a single compound. These data clearly indicate that the product is the intended compound, i.e., p-toluenesulfonic acid ester of 4-hydroxy-4'-p-toluenesulfonylbiphenyl.

EXAMPLE 6

An amount of 239 g (0.5 mole) of p-toluenesulfonic acid ester of 4-hydroxy-4'-p-toluenesulfonylbiphenyl obtained in Example 5 was treated in the same manner used in Example 2 to give 159 g of white crystalline powder. The product had a melting point of 242° C., a sulfur content of 9.9% and a hydroxyl value of 171.6 and gas chromatography measurement indicated that it was a single compound. These data clearly indicate that the product is the intended compound, i.e., 4-hydroxy-4'-p-toluenesulfonylbiphenyl.

EXAMPLE 7

There were charged, into a 500 ml inner volume autoclave having glass lining, 65.2 g (0.2 mole) of methanesulfonic acid ester of 4-hydroxy-4'-methanesulfonylbiphenyl prepared in Example 1-2, 150 g of water, 100 g of sulfolane and 10 g of sulfuric acid and the contents of the autoclave were heated and maintained at 180° C. for 4 hours with stirring. The pressure in the autoclave was about 9 kgf/cm$^2$ during the heat treatment. Then the contents were cooled, subjected to suction filtration, dried and recrystallized from xylene to give 47.2 g of white crystalline powder. The product Was consistent with the compound obtained in Example 2, i.e., 4-hydroxy-4'-methanesulfonylbiphenyl.

EXAMPLE 8

To a 1,000 ml inner volume, four-necked flask equipped with a stirring machine, a thermometer, a dropping funnel and a reflux condenser, there were added 340 g (2 moles) of 4-hydroxybiphenyl, 240 g (2.1 moles) of methanesulfonyl chloride and 50 g of dichloroethane and the contents of the flask were heated up to 100° C. with stirring. Then 120 g (0.8 mole) of trifuoromethanesulfonic acid to the contents over about one hour through the dropping funnel. After the dropwise addition, the temperature of the contents were raised up to 140° C. over 10 hours. The generation of hydrogen chloride gas was ceased and the reaction was completed after maintaining the contents at that temperature for 20 hours. There were charged, into a 2,000 ml inner volume autoclave having glass lining, the reaction mixture, 300 g of water and 200 g of sulfolane and the hydrolysis was performed at 150° C. for 8 hours. The contents of the autoclave were cooled, subjected to suction filtration and then the resulting filter cake was washed with 1,000 g of water. The filter cake was dried and then recrystallized from xylene to give 371 g of white crystalline powder. The product was consistent with the compound obtained in Example 2, i.e., 4-hydroxy-4'-methanesulfonylbiphenyl.

EXAMPLE 9

To a 2,000 ml inner volume, four-necked flask identical to that used in Example 5, there were added 1,200 g of dichloroethane, 340 g (0.7 mole) of p-chlorobenzenesulfonic acid ester of 4-hydroxybiphenyl prepared in the same manner used in Example 1 having a melting point of 176° C., 155 g (0.735 mole) of p-chlorobenzenesulfonyl chloride and 121.5 g (0.91 mole) of anhydrous aluminum chloride and the contents were heated with stirring so that they gently boiled. After 48 hours, the generation of hydrogen chloride gas was ceased and the condensation reaction was completed. Then the same procedures used in Example 5 were repeated to give 348 g of white crystalline powder. The product had a melting point of 178° C. and a sulfur content of 13.3% and gas chromatography measurement indicated that it was a single compound. These data clearly indicate that the product is the intended compound, i.e., p-chlorobenzenesulfonic acid ester of 4-hydroxy-4'-p-chlorobenzenesulfonylbiphenyl.

EXAMPLE 10

An amount of 259.5 g of the p-chlorobenzenesulfonic acid ester of 4-hydroxy-4'-p-chlorobenzenesulfonylbiphenyl prepared in Example 9 was treated in the same manner usd in Example 4 to give 169 g of white crystalline powder. The product had a melting point of 273° C., a sulfur content of 9.25% and a hydroxy value of 163 and gas chromatography measurement indicated that it was a single compound. These data clearly indicate that the product is the intended compound, i.e., 4-hydroxy-4'-p-chlorobenzenesulfonylbiphenyl.

EXAMPLE 11

To a 2,000 ml inner volume, four-necked flask of hard glass equipped with a stirring machine, a thermometer, a reflux condenser and an inlet port, 510 (3 moles) of 4-hydroxybiphenyl, 1,304 g (6.18 moles) of p-chlorobenzenesulfonyl chloride and 150 g of dichloroethane. When the contents of the flask were heated to about 70° C., most of the contents were molten and stirring was thus commenced. At this stage, 5 g (0.03 mole) of anhydrous ferric chloride was added thereto through the inlet port. After heating the contents to 80° C. for 5 hours, the generation of hydrogen chloride gas slightly went down. The first step of the condensation reaction was completed. The temperature of the contents was gradually raised from 100° C. to 140° C. and maintained at that temperature for about 10 hours. The generation of hydrogen chloride was almost ceased and the condensation reaction was finished. The reaction system was then treated in the same manner used in Example 3 to give 1,252 g of white crystaline powder. The product was consistent with the compound obtained in Example 9, i.e., p-chlorobenzenesulfonic acid ester of 4-hydroxy-4'-p-chlorobenzenesulfonylbiphenyl.

EXAMPLE 12

To a 2,000 ml inner volume, four-necked flask of hard glass equipped with a stirring machine, a thermometer and a reflux condenser, there were added 440 g (2.04 mole) of p-chlorobenzenesulfonyl chloride, 1,000 g of dichloroethane, 496 g (2 moles) of methanesulfonic acid ester of 4-hydroxybiphenyl prepared in Example 1-1 and 3.2 g (0.02 mole) of anhydrous ferric chloride. The contents of the flask were heated with stirring so that they gently boiled. The temperature of the contents was maintained at about 87° C. during the heat treatment. Hydrogen chloride gas generated during the reaction was released through the top of the reflux condenser and was properly treated.

After the contents of the flask were maintained under these conditions for 72 hours, the generation of hydrogen chloride gas was ceased and thus the rection was completed. The contents were cooled to 30° C., precipitates formed were filtered off, the resulting filter cake was washed with 500 g of methanol and then dried to give 795 g of white crystalline powder. The product had a melting point of 204° C. and a sulfur content of 15.1% and gas chromatography measurement indicated that it was a single compound. These data clearly indicate that the product is the intended compound, i.e , methanesulfonic acid ester of 4-hydroxy-4'-p-chlorobenzenesulfonylbiphenyl.

EXAMPLE 13

To a 2,000 ml inner volume, four-necked flask of hard glass equipped with a stirring machine, a thermometer, a dropping funnel and a reflux condenser, there were added 22 g of water, 1,200 g of methanol, 22 g (0.55 mole) of sodium hydroxide and 211 g (0.5 mole) of methanesulfonic acid ester of 4-hydroxy-4'-p-chlorobenzenesulfonylbiphenyl obtained in Example 12 and the contents of the flask was heated with stirring so that they gently boiled. After they were maintained at that condition for 5 hours, 140 ml of a 4N hydrochloric acid solution was dropwise added to the contents through the dropping funnel over about one hour. After cooling the contents to 30° C. or lower, they were filtered off through suction filtration and further the resulting filter cake was washed with 500 g of water.

After drying the cake, it was purified through recrystallization from dimethylformamide to give 169 g of white crystalline powder. The product had a melting point of 273° C., a sulfur content of 9.25% and a hydroxyl value of 163 and gas chromatography measurement indicated that it was a single compound. These data clearly indicate that the product is the intended compound, i.e., 4-hydroxy-4'-p-chlorobenzenesulfonyl-biphenyl.

As seen from the foregoing Examples, the method of the present invention permits the production of sulfones, whose preparation has conventionally been difficult, in high yield and high quality through relatively simple operations. Thus, useful sulfones having biphenyl structures can be supplied at a low cost an in an industrial scale.

We claim:

1. A method for preparing a sulfone represented by the following formula (5):

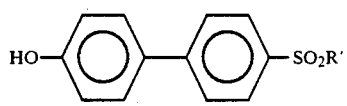

(5)

wherein R' represents a lower alkyl group, an aryl group or an aryl group whose nucleus has at least one substituent selected from the group consisting of a halogen atom selected from the group consisting of chlorine, bromine and fluorine, nitro group, a lower alkyl group, phenyl group and a phenyl group substituted with a halogen atom selected from the group consisting of chlorine, bromine and fluorine or an alkali metal salt thereof comprising:

the first step of condensing a sulfonic acid ester of 4-hydroxybiphenyl represented by the following formula (2):

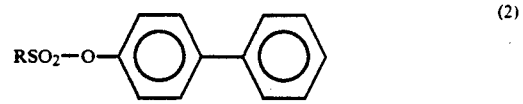

(2)

wherein R represents a lower alkyl group, an aryl group or an aryl group whose nucleus has at least one substituent selected from the group consisting of a halogen atom selected from the group consisting of chlorine, bromine and fluorine, nitro group, a lower alkyl group, phenyl group and a phenyl group substituted with a halogen atom selected from the group consisting of chlorine, bromine and fluorine with a sulfonyl chloride represented by the following formula (3):

(3)

wherein R' is the same as that defined above at a temperature of 0° to 200° C. in the presence of a Lewis acid selected from the group consisting of boron trifluoride, magnesium chloride, aluminum chloride, titanium chloride, ferric chloride, zinc chloride and tin chloride or a super-strong acid selected from the group consisting of fluorosulfonic acid, trifluoromethanesulfonic acid, pentafluoroethanesulfonic acid, phosphomolybdic acid, silicomolybdic acid, phosphotungstic acid and silicotungstic acid in an amount ranging from 0.1 to 300 mole % on the basis of the amount of the sulfonic acid ester of 4-hydroxybiphenyl or sulfonyl chloride to form a sulfone represented by the following formula (1):

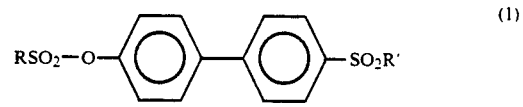

(1)

wherein R and R' are the same as that defined above; and the second step of saponifying said sulfone of the formula (1) according to one of the following: (i) at a temperature of not more than 10° C. in the presence of an alkali in an amount of at least two equivalents of the alkali per mole of the sulfone, (ii) at a temperature of 100° to 200° C. in the presence of an alkali in an amount of at least one equivalent of the alkali per mole of the sulfone, and (iii) at a temperature of 80° to 200° C. in the presence of an acid in an amount ranging from 0.01 to 0.5 equivalent of the acid per mole of the sulfone.

2. The method for preparing a sulfone or an alkali metal salt thereof according to claim 1 wherein the sulfone represented by the formula (5) is 4-hydroxy-4'-p-chlorobenzenesulfonylbiphenyl.

3. A method for preparing a sulfone represented by the following formula (5):

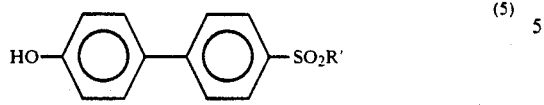

wherein R' represents a lower alkyl group, an aryl group or an aryl group whose nucleus has at least one substituent selected from the group consisting of a halogen atom selected from the group consisting of chlorine, bromine and fluorine, nitro group, a lower alkyl group, phenyl group and a phenyl group substituted with a halogen atom selected from the group consisting of chlorine, bromine and fluorine or an alkali metal salt thereof comprising:

the first step of condensing 4-hydroxybiphenyl with a sulfonyl chloride represented by the following formula (3):

R'SO$_2$Cl  (3)

wherein R' is the same as that defined above at a temperature of 0° to 100° C. in the presence of a Lewis acid selected from the group consisting of boron trifluoride, magnesium chloride, aluminum chloride, titanium chloride, ferric chloride, zinc chloride and tin chloride or a super-strong acid selected from the group consisting of fluorosulfonic acid, trifluoromethanesulfonic acid, pentafluoroethanesulfonic acid, phosphomolybdic acid, silicomolybdic acid, phosphotungstic acid and silicotungstic acid in an amount ranging from 0.1 to 300 mole % on the basis of the amount of the 4-hydroxybiphenyl or sulfonyl chloride;

the second step of condensing the sulfonic acid ester of 4-hydroxybiphenyl produced in the first step with a sulfonyl chloride represented by the following formula (3):

R'SO$_2$Cl  (3)

wherein R' is the same as that defined above at a temperature of 100° to 200° C. in the presence of a Lewis acid selected from the group consisting of boron trifluoride, magnesium chloride, aluminum chloride, titanium chloride, ferric chloride, zinc chloride and tin chloride or a super-strong acid selected from the group consisting of fluorosulfonic acid, trifluoromethanesulfonic acid, pentafluoroethanesulfonic acid, phosphomolybdic acid, silicomolybdic acid, phosphotungstic acid and silicotungstic acid in an amount ranging from 0.1 to 300 mole % on the basis of the amount of the sulfonic acid ester of 4-hydroxybiphenyl or sulfonyl chloride to form a sulfone represented by the following formula (4):

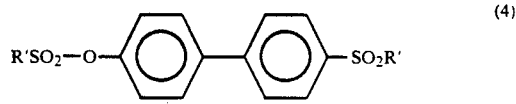

wherein R' is the same as that defined above; and
the third step of saponifying said sulfone of the formula (4) according to one of the following: (i) at a temperature of not more than 100° C. in the presence of an alkali in an amount of at least two equivalents of the alkali per mole of the sulfone, (ii) at a temperature of 100° to 200° C. in the presence of an alkali in an amount of at least one equivalent of the alkali per mole of the sulfone, and (iii) at a temperature of 80° to 200° C. in the presence of an acid in an amount ranging from 0.01 to 0.5 equivalent of the acid per mole of the sulfone.

4. The method for preparing a sulfone or an alkali metal salt thereof according to claim 3 wherein the sulfone represented by the formula (5) is 4-hydroxy-4'-p-chlorobenzenesulfonylbiphenyl.

* * * * *

UNITED STATES PATENT AND TRADEMARK OFFICE
CERTIFICATE OF CORRECTION

PATENT NO.  : 5,248,828
DATED       : September 28, 1993
INVENTOR(S) : Toranosuke Saito et al.

It is certified that error appears in the above-identified patent and that said Letters Patent is hereby corrected as shown below:

Claim 1, column 12, line 56, delete "10° C." and insert --100° C.--.

Signed and Sealed this

Twenty-ninth Day of March, 1994

Attest:

BRUCE LEHMAN

Attesting Officer          Commissioner of Patents and Trademarks